(12) United States Patent
Rothblatt

(10) Patent No.: US 12,322,495 B2
(45) Date of Patent: Jun. 3, 2025

(54) COMPUTING DEVICE FOR ENHANCING COMMUNICATIONS

(71) Applicant: Utasia Inc., Silver Spring, MD (US)

(72) Inventor: Martine Rothblatt, Silver Spring, MD (US)

(73) Assignee: Utasia Inc., Silver Spring, MD (US)

( * ) Notice: Subject to any disclaimer, the term of this patent is extended or adjusted under 35 U.S.C. 154(b) by 172 days.

(21) Appl. No.: 17/692,515

(22) Filed: Mar. 11, 2022

(65) Prior Publication Data

US 2022/0198798 A1 Jun. 23, 2022

Related U.S. Application Data

(63) Continuation of application No. 16/720,951, filed on Dec. 19, 2019, now Pat. No. 11,301,680, which is a continuation of application No. 14/724,982, filed on May 29, 2015, now Pat. No. 10,521,666, which is a continuation of application No. 13/966,686, filed on
(Continued)

(51) Int. Cl.
| | |
|---|---|
| *G09B 7/08* | (2006.01) |
| *A61B 5/00* | (2006.01) |
| *A61B 5/369* | (2021.01) |
| *G06F 1/16* | (2006.01) |
| *G16H 20/70* | (2018.01) |

(52) U.S. Cl.
CPC ............ *G16H 20/70* (2018.01); *A61B 5/369* (2021.01); *A61B 5/4088* (2013.01); *G06F 1/163* (2013.01)

(58) Field of Classification Search
CPC ....... A61B 5/369; A61B 5/4088; G16H 20/70
See application file for complete search history.

(56) References Cited

U.S. PATENT DOCUMENTS

| | | |
|---|---|---|
| 5,377,258 A | 12/1994 | Bro |
| 6,011,991 A | 1/2000 | Mardirossian |
| | (Continued) | |

FOREIGN PATENT DOCUMENTS

| | | |
|---|---|---|
| EP | 2 081 100 A1 | 7/2009 |
| JP | 07-204168 A | 8/1995 |
| | (Continued) | |

OTHER PUBLICATIONS

Deagle, Kerry, "Can brain-computer interface (BCI) systems facilitate communication in persons with Amyotrophic Lateral Sclerosis (ALS)?", Reviews, 2010, 1-6. www.uwo.ca/fhs/csd/ebp/reviews/2009-10/deagle.pdf. Downloaded on Apr. 21, 2014.
(Continued)

*Primary Examiner* — Kesha Frisby
(74) *Attorney, Agent, or Firm* — Foley & Lardner LLP

(57) ABSTRACT

A computing device for enhancing communications is disclosed. The computing device includes a memory configured to store data, a video camera configured to receive video input data, and a microphone configured to receive audio input data. The computing device also includes a processor that is configured to analyze the received video input data, the received audio input data, and the data stored in the memory. The computing device further includes a visual display device that is configured to output a visual display based on the processor analysis, and a speaker output device that is configured to output an audio signal based on the processor analysis.

20 Claims, 3 Drawing Sheets

Related U.S. Application Data

Aug. 14, 2013, now abandoned, which is a continuation of application No. 12/233,817, filed on Sep. 19, 2008, now abandoned.

(56) References Cited

U.S. PATENT DOCUMENTS

| | | |
|---|---|---|
| 6,309,361 B1 | 10/2001 | Thornton |
| 6,434,419 B1 | 8/2002 | Gevins |
| 6,463,321 B2 | 10/2002 | Granger |
| 6,466,232 B1 | 10/2002 | Newell et al. |
| 6,513,046 B1 | 1/2003 | Abbott, III et al. |
| 6,527,715 B2 | 3/2003 | Balkin et al. |
| 6,549,915 B2 | 4/2003 | Abbott, III et al. |
| 6,553,252 B2 | 4/2003 | Balkin et al. |
| 6,622,036 B1 | 9/2003 | Suffin |
| 6,743,167 B2 | 6/2004 | Balkin et al. |
| 6,842,877 B2 | 1/2005 | Robarts et al. |
| 6,878,111 B2 | 4/2005 | Kenknight |
| 6,996,261 B2 | 2/2006 | deCharms |
| 7,080,322 B2 | 7/2006 | Abbott et al. |
| 7,137,069 B2 | 11/2006 | Abbott et al. |
| 7,155,456 B2 | 12/2006 | Abbott |
| 7,761,414 B2 | 7/2010 | Freedman |
| 8,441,356 B1 | 5/2013 | Tedesco |
| 9,943,698 B2 | 4/2018 | Chase |
| 2001/0028309 A1 | 10/2001 | Torch |
| 2002/0076680 A1 | 6/2002 | Logan |
| 2002/0188217 A1 | 12/2002 | Farwell |
| 2004/0152060 A1 | 8/2004 | Ando |
| 2004/0210159 A1 | 10/2004 | Kibar |
| 2005/0163302 A1 | 7/2005 | Mock |
| 2005/0228785 A1 | 10/2005 | Wolcott et al. |
| 2006/0008785 A1 | 1/2006 | Clark |
| 2006/0009978 A1 | 1/2006 | Ma et al. |
| 2006/0093997 A1 | 5/2006 | Kearby |
| 2006/0173510 A1 | 8/2006 | Besio et al. |
| 2006/0184058 A1 | 8/2006 | Silberstein |
| 2007/0106127 A1 | 5/2007 | Alman |
| 2007/0191727 A1 | 8/2007 | Fadem |
| 2007/0299360 A1 | 12/2007 | Snyder |
| 2008/0122796 A1 | 5/2008 | Jobs |
| 2008/0138783 A1 | 6/2008 | Karkanias et al. |
| 2008/0208015 A1 | 8/2008 | Morris |
| 2009/0119154 A1 | 5/2009 | Jung |
| 2009/0247895 A1 | 10/2009 | Morikawa |
| 2010/0009324 A1 | 1/2010 | Owens |
| 2010/0062403 A1 | 3/2010 | Williams |
| 2010/0076334 A1* | 3/2010 | Rothblatt ............... G16H 20/70 600/544 |
| 2010/0285440 A1 | 11/2010 | Parikh |
| 2011/0015469 A1 | 1/2011 | Walter |
| 2011/0258570 A1 | 10/2011 | Bucolo |
| 2013/0072996 A1 | 3/2013 | Kilgard |

FOREIGN PATENT DOCUMENTS

| | | |
|---|---|---|
| JP | 2005-021569 A | 1/2005 |
| WO | WO 03/030734 A2 | 4/2003 |
| WO | WO 2008/059878 A1 | 5/2008 |

OTHER PUBLICATIONS

Kubler et al., Psych. Bullet., 2001, 127:358-275.

* cited by examiner

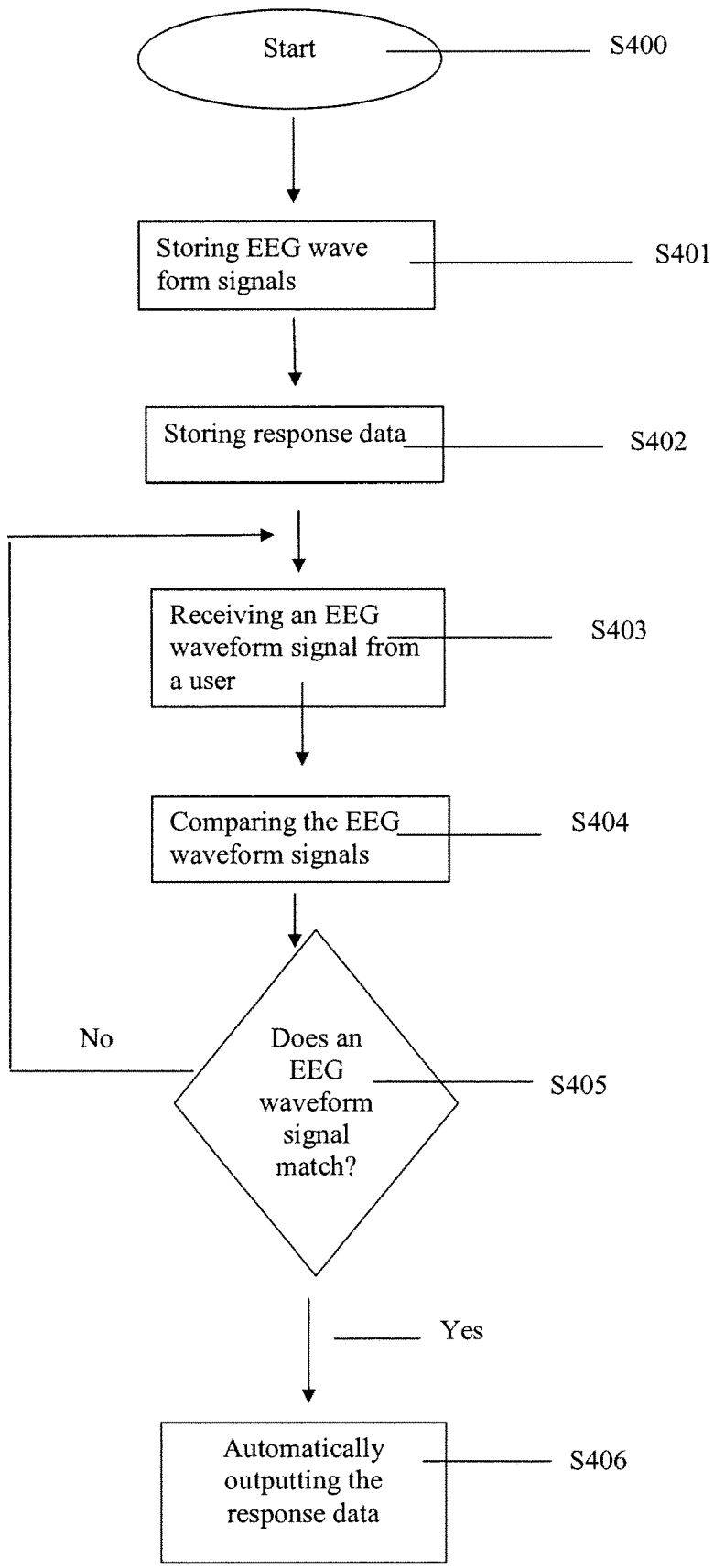

COMPUTING DEVICE FOR ENHANCING COMMUNICATIONS

CROSS-REFERENCE TO RELATED APPLICATIONS

This application is a Continuation of pending U.S. patent application Ser. No. 16/720,951 filed on Dec. 19, 2019, which is a Continuation of U.S. application Ser. No. 14/724,982, filed May 29, 2015, which is a Continuation of U.S. application Ser. No. 13/966,686, filed Aug. 14, 2013, which is a Continuation of U.S. application Ser. No. 12/233,817, filed on Sep. 19, 2008. The content of all these applications is incorporated herein by reference in its entirety.

BACKGROUND OF THE INVENTION

1. Field of the Invention

Embodiments of the present invention relate to apparatus, systems and methods for improving the quality of life of an individual suffering from a debilitating disease as well as members of interest affected by the sufferer's diminished capacity.

2. Description of the Related Art

Debilitating diseases which affect a person's mental capacity are especially difficult to endure, both for the individual suffering from the disease as well as family members, friends and caregivers who must care for the individual. One form of a mentally debilitating disease is dementia. Dementia is a brain disorder that seriously affects a person's ability to carry out daily activities. The most common form of dementia among older people is Alzheimer's disease, which initially involves the parts of the brain that control thought, memory, and language. In its early stages, memory loss, shown as a difficulty to remember recently learned facts, is the most common symptom, although it is often initially misdiagnosed as age-related memory-loss or stress. Later symptoms include confusion, anger, mood swings, language breakdown, long-term memory loss, and the general withdrawal of the sufferer as his or her senses decline. Each individual experiences the symptoms of Alzheimer's disease in unique ways. The duration of the disease is between 5 and 20 years.

Currently, there is no cure for Alzheimer's disease. Also, there are no effective ways for an Alzheimer's disease sufferer to effectively interact with family and friends at the various stages of the disease.

Therefore, a need exists for an apparatus, system and method that allows an Alzheimer's disease suffer to effectively interact with family, friends, caregivers, etc. at the various stages of the disease.

SUMMARY OF THE DISCLOSURE

Accordingly, an Alzheimer's cognitive enabler is disclosed that allows an Alzheimer's disease suffer to effectively interact with family, friends, caregivers, etc. at the various stages of the disease.

According to one embodiment of the present invention, a computing device that enables user interaction when the user is in a mentally debilitating state includes a memory configured to store electroencephalogram (EEG) waveform signals. The EEG waveform signals are generated by associated recognition data. Response data is generated based on the associated recognition data and stored in memory. An input component is configured to receive an EEG waveform signal from a user. A processor is configured to compare the received EEG waveform signal with the stored EEG waveform signals to determine if the received EEG waveform signal matches a stored EEG waveform signal. An output component is configured to automatically output the response data generated by the associated recognition data based on the determination from the processor.

According to another embodiment of the present invention, a computer system that enables user interaction when the user is in a mentally debilitating state includes a computing device and a server computer. The computing device includes a memory, an input component, a processor and an output component. The memory is configured to store EEG waveform signals. The EEG waveform signals are generated by associated recognition data. Response data is generated based on the associated recognition data and stored in memory. The input component is configured to receive an EEG waveform signal from a user. The processor is configured to compare the received EEG waveform signal with the stored EEG waveform signals to determine if the received EEG waveform signal matches a stored EEG waveform signal and the output component is configured to automatically output the response data generated by the associated recognition data based on the determination from the processor. The server computer is configured to update EEG waveform signals, associated recognition data and response data stored in the memory of the computing device.

According to a further embodiment of the present invention, a method for enabling user interaction when the user is in a mentally debilitating state includes storing electroencephalogram (EEG) waveform signals, whereby the EEG waveform signals are generated by associated recognition data. The method also includes the steps of storing response data generated based on the associated recognition data and receiving an EEG waveform signal from a user. The method further includes the steps of comparing the received EEG waveform signal with the stored EEG waveform signals and determining that the received EEG waveform signal matches a stored EEG waveform signal. The method also includes the step of automatically outputting the response data generated by the associated recognition data based on the determining step.

BRIEF DESCRIPTION OF THE DRAWINGS

These and other features, aspects and advantages of the present invention will become better understood with regard to the following description, appended claims and accompanying drawings where:

FIG. 3 is a flowchart depicting steps performed within the ACE device in accordance with one embodiment of the present invention.

DETAILED DESCRIPTION

Unless otherwise specified, "a" or "an" means "one or more."

Recent advancements in non-invasive electroencephalogram (EEG) waveform monitoring for the gaming industry have enabled a significant array of EEG waveform signals to be associated with ideational content. In addition, recent advancements in image and voice recognition technologies have enabled these technologies to be used easily with personal computers. These technologies, however, have been limited to being practiced in their own particular industry and have not been linked together to assist individuals suffering from Alzheimer's disease. In general, an Alzheimer's disease patient is mentally capable of more than they can articulate or express. According to an embodiment of the present invention, an Alzheimer's cognitive enabler (ACE) allows the Alzheimer's disease patient to draw upon his or her less-affected cognitive waveforms to trigger recognition and conversation functions that are blocked by beta amyloid plaque in the brain, but can be made available on the ACE. In other words, the ACE may be equated to or conceptualized as a "cognitive wheelchair" providing mental assistance as compared to physical assistance provided by a conventional wheelchair.

Figure 1:
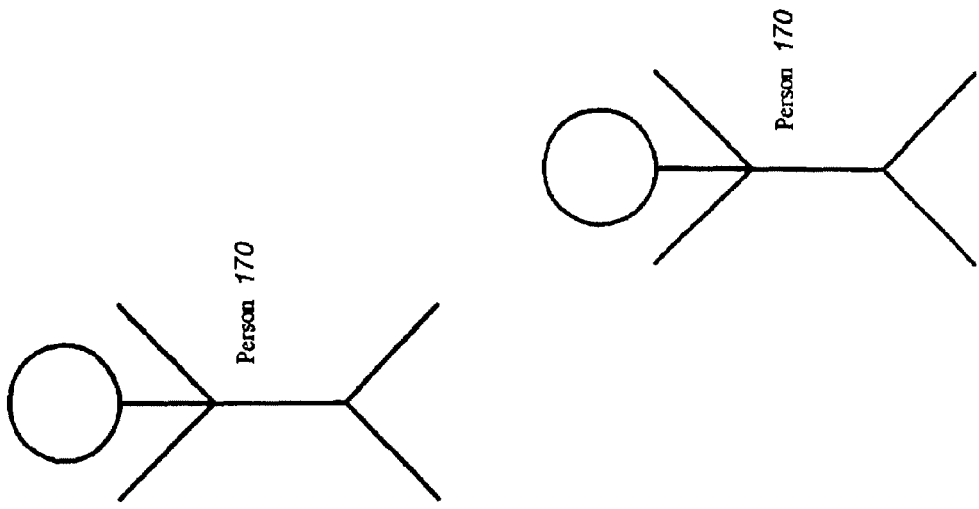
FIG. 1 illustrates a user with an embodiment of the Alzheimer's Cognitive Enabler (ACE) device of the present invention.
Figure 1:
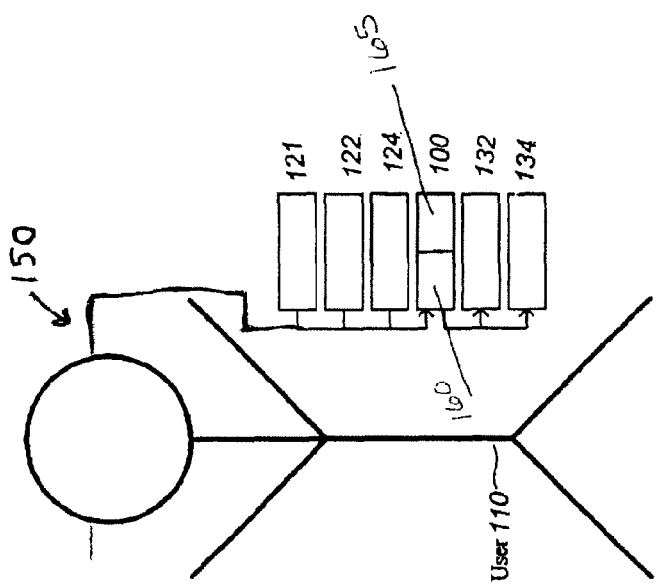

Consider, for example, ACE device 100 being carried by user 110 (i.e., an Alzheimer's patient) in FIG. 1. In this exemplary embodiment illustrated in FIG. 1, the ACE device 100 has access to input devices such as an EEG device 150, video camera 121, microphone 124, and input device 122 (e.g., a keyboard, a hand-writing recognition device, etc.). The ACE device 100 also has access to a visual display device 132 and a speaker output device 134. In some embodiments of the present invention, the input and output devices may be integrated together with the ACE device 100 into a single device, while in alternative embodiments the ACE device 100 may be a separate device that has the ability to accept input from and provide output to (e.g., via physical or wireless connections) any of a variety of devices which may be accessible (e.g., carried by the user or located nearby in the environment). The ACE device 100 further includes a processor 160 for processing information stored in its memory 165 as discussed in greater detail below.

The invention is further illustrated by, though in no way limited to, the following particular embodiments and examples. In the example illustrated in FIG. 1, a variety of situations are illustrated for which user 110 may wish to store information that can be later used to assist the user 110 to interact with persons 170. According to one embodiment of the present invention, the ACE device 100 is prescribed for user 110 at the user's first sign of cognitive decline. During this still relatively healthy stage, the Alzheimer's patient, family member(s) and/or caregivers would load the ACE device 100 with the patient's salient images, voices data, memories, etc. and associated EEG waveforms. Via artificial intelligence technology, however, it is not critical that every bit of data has an associated EEG waveform. For example, there may be an EEG waveform associated with the image of a patient's son. However, there need not be an EEG waveform associated with an image of the son together with the patient. The artificial intelligence program running the ACE device 100 uses relational database technology to bring together related images after an index image is EEG triggered. More generally, the ACE device 100 is configured to conduct a normal conversation with a person based on stored data and advanced artificial intelligence-based chatbot software upon an EEG waveform associated with just recognition of the person. In general, any EEG waveform will trigger some conversational capability out of the ACE device 100, with such conversational capability being as close to the motivations that gave rise to the EEG waveform as the stored associations permit. While wearing EEG device 150, the Alzheimer's patient is able to train the ACE device 100 to react as he or she would in given situations when interacting with others. Thereafter, once the disease has progressed, the ACE device 100 can be used to interact with others on behalf of the Alzheimer's patient using images and sound recognition routines, conversational software and patient-specific settings previously stored and continuously updated as discussed in greater detail below.

For example, upon encountering person 170 for the first time, the user 110 may wish to store a variety of information about the person for later recollection. In particular, the user 110 can use the video camera 121 and microphone 124 to capture video and audio recordings of the encounter. The user 110 can also use the video camera 121 to capture other current information about the environment which may assist in later recollection about the encounter, such as a video image of the location in which the encounter occurred. In addition, the user 110 can use the microphone 124 to record dictated information about the person 170, such as the person's name, address, e-mail address, phone number, etc. The ACE device 100 can then store this dictated information as an audio recording, or can instead perform voice recognition on the dictation in order to produce a textual version of the information. Alternately, the user 110 can provide some, or all of the information about the person to the ACE device 100 directly as text via text input device 121. In other embodiments, the user 110 can provide information to the ACE device 100 via any other available input means, such as transmitted information from a portable device (not shown) that the person might be carrying (e.g., another ACE device). After receiving and processing the various information about the encounter with the person 170, the ACE device 100 associates the various information with the received EEG waveform signal from the EEG device 150.

According to one embodiment of the present invention, the ACE device 100 is configured such that an Alzheimer's patient who sees person 170 again, but fails to recognize him, could automatically trigger an appropriate greeting for person 170 based on the EEG waveform generated when the Alzheimer's patient's see that person again but is unable to recognize him.

The ACE device 100 may be in the form of a general-purpose body-mounted wearable computer worn by user 110. Many wearable computers travel with the user, such as being strapped or attached to a user's body or clothing or being mounted in a holster. The wearable computer has a variety of user-worn user input devices including the microphone 124, a hand-held flat panel display with character recognition capabilities, and various other user input devices 222. Similarly, the computer has a variety of user-worn output devices that include the hand-held flat panel display, an earpiece speaker, an eyeglass-mounted display, etc. In addition to the various user-worn user input devices, the computer can also receive information from various user sensor input devices and from environment sensor input devices, including the video camera 121. The ACE device 100 can receive and process the various input information and can present information to the user 110 on the various output devices. Thus, as the user 110 moves about in various environments, the ACE device 100 receives various input information from the input devices that can be stored.

The general-purpose body-mounted wearable computer may include a touch screen feature (which may approximate the size of a human head, but could be any size, for example) that enables the ACE device 100 to respond to tactile as well as audio and video inputs. For example, if the Alzheimer's patient was in a late stage of the disease, the patient's omnipresent, naturally moving image on the touch screen could be kissed, and the programming features of the ACE device 100 would recognize that input and respond in the Alzheimer patient's voice, with a reply such as "THANK YOU FOR THE KISS GRANDSON."

Those skilled in the art will appreciate that specialized versions of the body-mounted computer can be created for a variety of purposes. Those skilled in the art will also appreciate that a variety of such physiological conditions can be monitored, and that other specialized versions of the device can similarly be implemented.

System Environment

Figure 2:
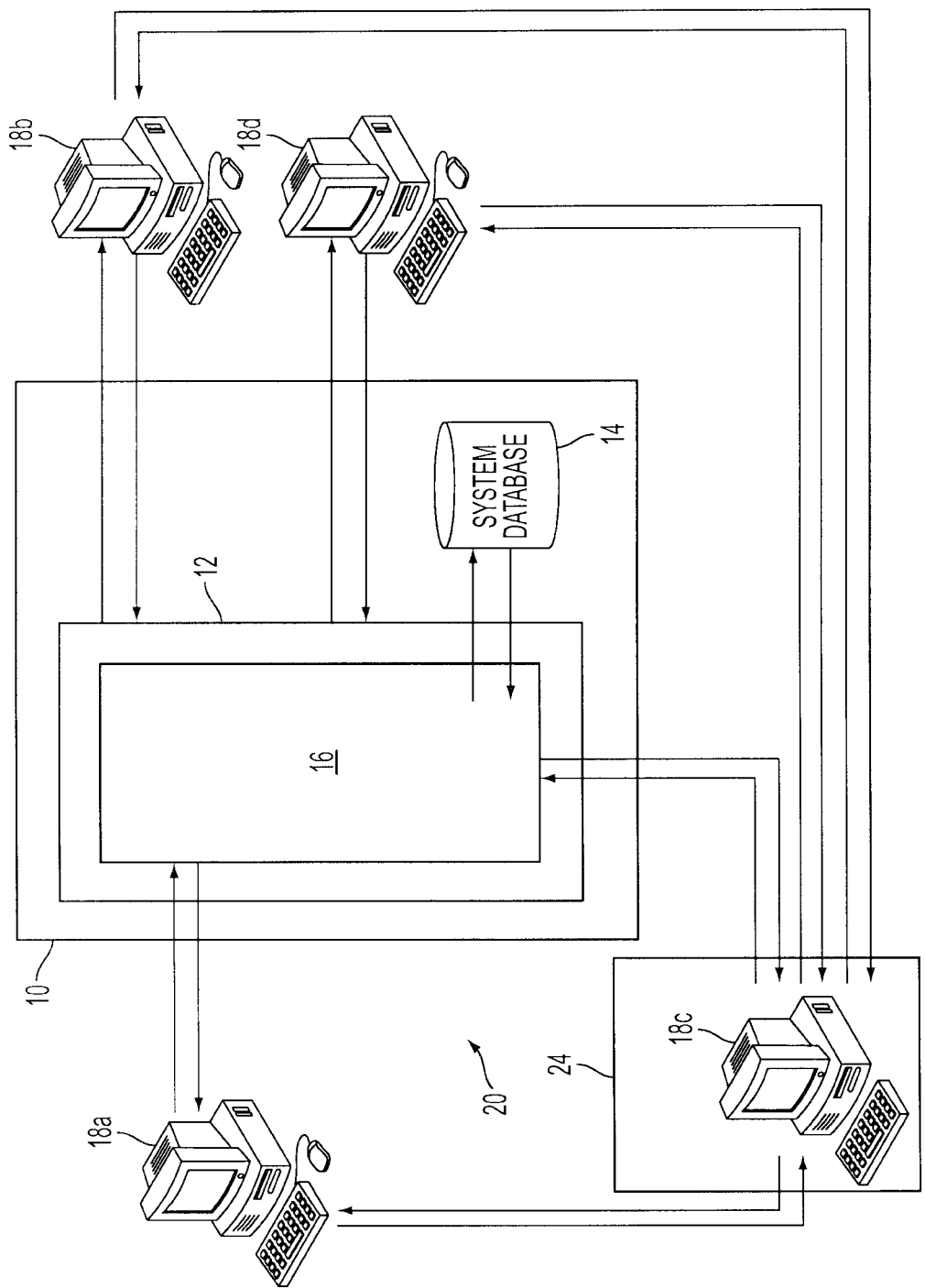
FIG. 2 illustrates an operating environment in which the ACE device, system and method of the present invention may operate.

Referring to FIG. 2, an ACE system and method of the present invention operates primarily in a computer network environment. In this embodiment, the ACE system 20 includes a program system administration site 10 which includes server computer 12 and a system database 14 and a number of workstations 18 that communicate with the server computer 12. The workstations 18 may be used by patients/caregivers 18a, family members 18b or friends 18c or any other system participant 18d. According to an embodiment of the present invention, the workstation 18 may be a stand alone personal computer (PC) based system with wireless internet connectivity, and Smart Phones with Wi-Fi connectivity to an off-site server, the same as the ACE device 100. The off-site server may provide software upgrades, act as a repository for certain database functions and provide diagnostic functions. For example, the wireless-linked feature of the ACE device 100 and the ACE system 20 helps to ensure that no data is lost in the event of a failure, theft, breakage or loss of the ACE device 100. At user-settable periods all data from the ACE device 100 is automatically uploaded to server computer 12 and then to system database 14 for safe storage. This stored data can be readily downloaded into a replacement ACE device. The personal computer typically will require a video monitor, sound and video cards. Alternatively, the workstation 18 may be any device capable of interacting with a computer network, including such devices as personal digital assistance (PDA) and cellular phones.

Additional system requirements include a PC compatible video camera, PC compatible directional microphone, speakers, and a Blue Tooth commercial EEG headset. In the caregiver/institutional setting, a tablet PC, and voice activated microphones may be required in addition to the above. Embodiments of the present invention also may require on-site training and a patient support facility 24 in some cases or the patient may require assistance in utilizing the invention, in both instances the ACE system 20 is amenable to additional users assisting the patient in providing the input or in training the patient in utilizing the supplemental system input devices. Resident on the sever computer 12 of the ACE system 20 is an Alzheimer's disease recognition program 16. Also, with the wireless-linked feature of the ACE device 100 and ACE system 20, responsiveness of the ACE device 100 to be continually improved via new software downloaded from server computer 12. At the server computer 12, software will analyze the ACE patterns of interaction the are uploaded each day to tune the ACE device's 100 program to better match the Alzheimer's patient's healthy pattern of conversation. According to one embodiment of the present invention, server 12 has installed therein, newer versions of conversational software that are more sophisticated in replicating normal conversational patterns. Such software is configured to review saved conversations between the patient and family to identify errors and adjust conversational parameters. This is analogous to how "auto-tune" software works with digital music, in that a person's voice can be analyzed for being off-tune and corrected.

System Training and Data Base Elements

According to one preferred embodiment of the present invention, the ACE device 100 and ACE system 20 are trained via patient interaction in each of the following instances: recording the patient's voice, obtaining varying minutes of digital video of the patient's facial expressions (speaking, laughing, and joy, sadness) to obtain a viseme database. As used throughout this specification, a viseme is defined as a unit of speech in the visual domain; how ones face forms words and expressions. The ACE device 100 and ACE system 20 build a lexicon of patient's visemes from video taping the patient. In the case where the patient cannot participate, the lexicon is built synthetically. In the synthetic process, the patient's face is photographed in high definition, for example, and donor visemes are digitally overlaid onto the photographed face of the patient and the result is akin to live animation.

According to one embodiment of the present invention, videotaping can be performed by trained staff, a caregiver, etc. The patient may also construct, or be assisted in constructing a database of family members and friends (Family/Friends) with whom the patient would wish to interact. The database may also include the contact information for caregivers and health care providers. According to the operation of the present invention, voice samples of these individuals may be collected from Wi-Fi capable cell phone interactions, as well as prearranged voice recording conducted by training staff. Afterwards, the patient may construct or be aided in constructing, or have constructed by the training staff, a database of responses for their phone (cellular and landline) and PC systems, as well as establishing the pre-sets for when the system responds for them.

According to an exemplary embodiment of the present invention, baseline voice samples of the patient may be used for Alzheimer analysis. The patient may be instructed by a staff member in the training and use of the EEG device 150. As stated previously, the EEG device 150 serves as an auxiliary data input tool and data collection device for the ACE device 100 and ACE system 20 with the EEG signals serving in place of the PC's mouse, acting as a drawing and pointing/selection agent on the screen, and one capable of dragging and dropping screen based objects. According to an alternative embodiment of the present invention, if the EEG signals are confused, or unrecognized, the software is configured to default to running as if the appropriate EEG signal was triggered. For example, if "daughter" has a specific EEG, signal but it is not recognized, it will be possible for "daughter" to specify that it is the daughter visiting the patient, and then the ACE device 100 will converse as if the EEG signal for "daughter" had been triggered. Familiarity with the EEG device 150 will also assist the patient in accessing the device and system as the patient's health declines. Baseline EEG samples obtained from patient use may be uploaded to the server 12 and the data may be then analyzed. The patient may be trained to use the voice recognition software as an auxiliary data entry tool. This will allow the patient to more readily enter his or her autobiographical memories, and to use the PC more fully in conjunction with the EEG device 150. Voice samples from the usage may be utilized for voice synthesis as well as diagnostic analysis.

Profiles

According to one preferred implementation of the present invention, the data collected through phone conversations and interviews with the patient and the patient's Family/Friends may be utilized to assist in constructing affirmative conversations for the ACE device 100 and ACE system 20 to deploy. In the instance that the patient is sufficiently incapacitated and unable to participate in the interview process, in a preferred implementation of the present invention, staff psychologists may conduct interviews with Family/Friends, review personal material and construct a patient autobiographical inventory that will serve as the basis for constructing a conversational database and the autobiographical database stored either in the ACE device 100 or stored remotely on the ACE system 20.

According to the operation of the ACE device 100 and the ACE system 20, if a user 110 is unable to recognize a person initiating a conversation, the EEG waveform signal generated from the EEC device 150 is used to retrieve the correct responses. According to an alternative operation of the ACE device 100 and ACE system 20, voice and face recognition software is used to identify the initiator of a conversation and then the ACE device 100 and ACE system 20 supplies a correct response set based on the recognition of the initiator of the conversation. In the preferred implementation of the present invention, the response is profiled based upon the historical psychodynamics between that individual and the patient. The ACE device 100 and ACE system include a profiling methodology which is a psychological framework employed to maximize the therapeutic investment of energy into the suspense of disbelief experienced by the patient's Friend/Family in interacting with a patient avatar. According to the present invention, a patient avatar is defined as an audio construct of the patient, one that will have the patient's face, facial expression and voice. In the instance that the patient was an early participant of the system and partook in the system training, the patient avatar will appear on the monitor speaking in the patient's own voice, and to a very large degree, with the patients' own facial expressions. If the patient was unable to participate, the voice will be gender appropriate and pitch and tone balanced. According to an exemplary embodiment of the present invention, the facial expression may be human and warm and the face will be that of the patient.

According to an alternative embodiment of the present invention, the ACE device 100 and ACE system 20 may include an emotion software engine that is based upon actual digitally sampled emotions from an Alzheimer's patient. According to this implementation of the present invention, the ACE device 100 and ACE system 20 are configured to portray realistic emotions of the Alzheimer's patient, triggered by EEG waveform signals and/or program-analyzed semantic cues in a conversational software engine.

According to one embodiment of the present invention, the conversational database generates an appropriate conversational segment in response to a unique speaker from the information stored in the system database 14 or in the memory of the ACE device 100 and then further processed. An example conversation is provided below:
SARAH: HI NANA, HOW ARE YOU?
NANA: I'M DOING SO-SO TODAY PRECIOUS, HOW IS YOUR LITTLE JO-JO?
Sarah, the grand-daughter, is recognized by the ACE device 100 or the ACE system 20, either by the associated EEG waveform, voice recognition software or face recognition software, the conversation generation then looks up Sarah, recognize her grandmother's pet name for her and that she has a pet named Jo-jo.

System Inputs

As part of the ACE device 100 and ACE system 20, inputs according to an embodiment of the present invention, including videotaping of a patient in scripted conversation conducted by training staff. According to one preferred implementation of the present invention, this may be held over multiple sessions of 15 minute duration totaling 60 minutes in aggregate, for example. The sessions are designed to capture the patient in a variety of emotional responses and facial patterns. The trainer/technician performing the video taping in addition to following the script may be trained in how to provoke the various emotive responses desired in order to capture a variety of facial expression of the patient. The resulting video is then processed into the viseme database for the patient avatar as discussed above. For example, high quality head shots of the patient's designated Family/Friends may be taken by the training staff and input into the ACE device 100 and ACE system 20 for the facial recognition component. The training staff may also sample Family/Friend vocal recordings for input into the voice recognition component. In the event that the patient is of diminished capacity and cannot withstand the rigors of the interview process, the trainer may take high definition images of the patient's face. Visemes may then be constructed synthetically from the images. The process is one of overlaying the patients face over a "digital donor", one carries out the process of mapping say, trainer Mary's visemes, removing Mary's characteristic facial features leaving behind a dynamic template, and then mapping the patient's facial features onto the template. This may be a one time process, completed on site by the training staff.

System Output

As part of the ACE device 100 and ACE system 20 outputs according to an embodiment of the present invention, text, audio-visual, or audio responses through the patient's phone system (land as well as cellular) and PC/PDA/Smartphone either at the patient's request or at a predetermined setting in response to the diagnostic data gathered from the patient may be output. Video may be processed and synchronized with the patient's visemes to produce a patient avatar. According to one preferred implementation of the present invention, the processing may be conducted by training staff onsite. The ACE device 100 and ACE system 20, when prompted by the initiator, may then cue the conversational database load either in the system database 14 or locally in memory of the ACE device 100 for the initiator and prepare to integrate the speech synthesis engine with the patient avatar in response to the initiators spoken word.

System Diagnostics

According to one preferred embodiment of the present invention, voice data obtained from voice control of the PC and from cellular conversations may be analyzed for early onset of the Alzheimer's using currently established diagnostic benchmarks developed for voice recognition technology and the indicia of Alzheimer's disease. This data set may be compared against baseline voice data collected at the patient's initial use of the system. EEG waveform data collected from the patient may be analyzed using currently established protocols for the prediction of or indicia of Alzheimer's disease. Through these two processes a reasonable degree of statistical likelihood exists in being able to understand the degree of incapacity of the patient at a given time and whether to invoke the patient's choices in terms of responding to phone calls or PC communications, or in calling for caregivers, health providers or family members.

System and Program Model

According to a further preferred embodiment of the present invention, ACE system 20 is a system platform that is designed to assist a patient diagnosed in the pre-onset stages of Alzheimer's disease through the later stages of the disease. In the pre-onset stage, the preferred model envisions a patient's interacting directly with the ACE device 100 and ACE system 20, providing inputs both for system training, patient diagnosis and patient memory storage. As the patient becomes infirmed, or feels unable to complete or attend to specific communication based tasks, the device and system provide responses for the patient. If the patient becomes institutionalized or requires a caregiver and reaches a stage of diminished conversational capacity, the ACE device 100 and ACE system 20 are configured to recognize a vocal prompt and or the face of a member from the Family/Friend indexed in the database 14 or local memory, which will initialize the device and system and will commence conversation with the indexed individual.

In the pre-onset stage of Alzheimer's disease, the patient interacts with the device and system through a number of dimensions. Phone conversations provide profile data for the Family/Friend database-namely, the individuals within the database, voice samples, frequency and duration of interaction; cellular phone data is transmitted via Wi-Fi to the server 12 for storage and analysis. PC based activities may be gradually controlled by supplemental devices, viz., the patient's oral commands (voice recognition) and through EEG waveform based commands. Data collected from the device and system may be transmitted to the server 12 for diagnostic analysis and for use in the patient avatar. If the patient feels fatigued, or if the EEG waveform based diagnostics advise the patient or the patient's caregiver that the patient is entering a deficit, the device and system may be engaged by default or by the patient's choice to intervene on any or all communication channels available to the patient. If the perceived deficit reaches a predetermined threshold, the device and system is configured to alert caregivers, healthcare providers, and family members and friends as desired.

In the intermediate stage of Alzheimer's disease, the patient has some capacity for conversation, or may easily feel fatigue. According to a preferred implementation of the present invention, the patient may wear and may interact with the ACE device and ACE system through the EEG device 150 and may guide the conversation with Family/Friends, selecting conversational elements from the conversational database or elements from his or her autobiographical database via a tablet PC. In this implementation of the present invention, the patient may also turn the patient avatar on or off. The pre-sets established will determine whether the patient is in a state to make the determination.

When a patient is in a state of decline such that self sustaining conversation is either a burden to the patient or a mental impracticality, the ACE device and system is configured to intervene between the patient and family member, or the patient and the patient's friend. The patient is present, juxtaposed with a video monitor of either the ACE device or ACE system. In one preferred implementation of the present invention, one speaker at a time engages the patient, with each speaker wearing a voice activated microphone. Upon speaking to the patient, the device and system is activated via voice and facial recognition using the software provided therein; the patient avatar displays recognition, and enters into a conversation with the initiator. The patient avatar is configured to converse approximately as one would expect an elderly family member: short answers, of durations 20 seconds or less, and for a total conversation length of no more than five minutes per family participant, for example.

According to an embodiment of the present invention, the conversations with the same party normally will not repeat the same content during the next conservation if (i) the original database is sufficiently robust and (ii) the conversation doesn't duplicate the content, for example. Even in the second instance, for example, there is no assurance that the content of the patient avatar's content would be the same. The content of the conversation may be uploaded to a server, such as server 12 for diagnostic analysis. Specific events referenced by the patient avatar may be accessed by the Family/Friend by accessing the autobiographical database events referenced for that day.

Telemetry

According to an embodiment of the present invention, the ACE device and system are also configured to monitor patient pain and mood levels via EEG waveform signals output as well as a standard set of outputs (e.g., heartbeat, pulse rate, blood pressure, etc.). All data collected is available to the patient's health care providers and approved subscribers historically and in real-time via Wi-Fi (PC/Smartphone/PDA) or a remote server.

FIG. 3 is a flowchart depicting steps performed within the ACE device in accordance with one embodiment of the present invention. The process begins from a start state S400 and proceeds to process step S401, wherein EEG waveform signals are stored in memory. The EEG waveform signals are generated by associated recognition data. At process step S402, response data generated based on the associated recognition data is also stored in memory. After the information has been stored, at process step S403, an EEG waveform signal from a user is received. After receiving the EEG waveform signal, the process proceeds to process step S404 where the received EEG waveform signal is compared with the stored EEG waveform signals. After the comparison step, the process proceeds to decision step S405 where it is determined whether or not the received EEG waveform signal matches a stored EEG waveform signal. If the received EEG waveform signal matches one of the stored EEG waveform signals, the process proceeds to process step S406 where the response data generated by the associated recognition data is automatically outputted, otherwise, the process returns to process step S403.

Alzheimer's disease is characterized by a slow, gradual decline in cognition which cause great sorrow and diminished quality of life to the Alzheimer's disease sufferer as well as his or her family. The ACE device, system and method can significantly ameliorate the diminished quality of life.

Based on this description of exemplary embodiments, other embodiments will be readily apparent to one of skill in the art. Thus, these exemplary embodiments should be considered as limiting the scope, which is defined according to the following claims.

What is claimed is:

1. A system comprising:
an electroencephalogram (EEG) device to receive EEG data;
a memory; and
one or more processors to perform operations to:
   maintain, in the memory, a conversational database mapping each EEG signal of a plurality of EEG signals of a patient to (i) a corresponding individual of a plurality of individuals with whom a patient is likely to interact and (ii) a corresponding response data set of a plurality of response data sets;
   receive, from the EEG device, responsive to an encounter of the patient with a first individual of the plurality of individuals, a first EEG signal of the patient;
   determine a second EEG signal in the conversational database that matches the first EEG signal received from the EEG device;
   determine a conversational response based on a response data set mapped to the second EEG signal in the conversational database; and
   output the conversational response on behalf of the patient responsive to the encounter of the patient with the first individual.

2. The system of claim 1, wherein the conversational response includes an audio signal and the system further comprises a speaker output device to output the audio signal.

3. The system of claim 1, wherein the conversational response includes a textual signal and the system further comprises a display device to render the textual signal.

4. The system of claim 1, further comprising a microphone configured to receive audio signals.

5. The system of claim 4, wherein the conversational database further includes baseline voice samples of each of the plurality of individuals, and the one or more processors perform operations to:
   receive, via the microphone, an audio signal responsive to the first individual initiating a conversation with the patient; and
   identify the first individual based on the received audio signal and the baseline voice samples.

6. The system of claim 1, wherein the conversational database includes a plurality of facial expressions of the patient, each facial expression associated with a corresponding individual of the plurality of individuals.

7. The system of claim 6 further comprising a display device, wherein the one or more processors perform operations to cause the display device to render a facial expression of the patient associated with the first individual.

8. The system of claim 1, wherein the one or more processors perform operations to output the conversational response through a smartphone of the patient.

9. The system of claim 1, wherein the one or more processors perform operations to monitor one or more physiological conditions of the patient based on EEG signals of the patient received via the EEG device.

10. The system of claim 1, wherein the one or more processors perform operations to identify the first individual using facial recognition.

11. A method comprising:
   maintaining, in a memory, a conversational database mapping each electroencephalogram (EEG) signal of a plurality of EEG signals of a patient to (i) a corresponding individual of a plurality of individuals with whom a patient is likely to interact and (ii) a corresponding response data set of a plurality of response data sets;
   receiving, by one or more processors from an EEG device, responsive to an encounter of the patient with a first individual of the plurality of individuals, a first EEG signal of the patient;
   determining, by the one or more processors, a second EEG signal in the conversational database that matches the first EEG signal received from the EEG device;
   determining, by the one or more processors, a conversational response based on a response data set mapped to the second EEG signal in the conversational database; and
   outputting, by the one or more processors, the conversational response on behalf of the patient responsive to the encounter of the patient with the first individual.

12. The method of claim 11, wherein the conversational response includes an audio signal and the method further comprises outputting the audio signal through a speaker output device.

13. The method of claim 11, wherein the conversational response includes a textual signal and the method further comprises rendering the textual signal on a display device.

14. The method of claim 11, wherein the conversational database further includes baseline voice samples of each of the plurality of individuals, and the method comprising:
   receiving, via a microphone, an audio signal responsive to the first individual initiating a conversation with the patient; and
   identifying the first individual based on the received audio signal and the baseline voice samples.

15. The method of claim 11, wherein the conversational database includes a plurality of facial expressions of the patient, each facial expression associated with a corresponding individual of the plurality of individuals.

16. The method of claim 15 further comprising causing a display device to render a facial expression of the patient associated with the first individual.

17. The method of claim 11, comprising outputting the conversational response through a smartphone of the patient.

18. The method of claim 11, further comprising monitoring one or more physiological conditions of the patient based on EEG signals of the patient received via the EEG device.

19. The method of claim 11, further comprising identifying the first individual using facial recognition.

20. The method of claim 11, wherein the conversational database includes an autobiographical inventory of the patient storing data about the plurality of individuals.

* * * * *